(12) United States Patent
Charlez et al.

(10) Patent No.: US 8,430,866 B2
(45) Date of Patent: Apr. 30, 2013

(54) PLEURAL DRAINAGE DEVICE AND VALVE FOR SUCH

(75) Inventors: Jarl Charlez, Askim (SE); Mikael Charlez, Mölndal (SE)

(73) Assignee: Medela Holding AG, Baar (CH)

( * ) Notice: Subject to any disclaimer, the term of this patent is extended or adjusted under 35 U.S.C. 154(b) by 663 days.

(21) Appl. No.: 12/664,336

(22) PCT Filed: Jun. 29, 2007

(86) PCT No.: PCT/SE2007/050483
§ 371 (c)(1),
(2), (4) Date: Dec. 11, 2009

(87) PCT Pub. No.: WO2009/005424
PCT Pub. Date: Jan. 8, 2009

(65) Prior Publication Data
US 2010/0174270 A1    Jul. 8, 2010

(51) Int. Cl.
*A61M 1/00* (2006.01)
(52) U.S. Cl.
USPC ............................................. 604/540
(58) Field of Classification Search .......... 604/540
See application file for complete search history.

(56) References Cited

U.S. PATENT DOCUMENTS

| | | | | |
|---|---|---|---|---|
| 315,521 A | * | 4/1885 | Lord et al. | 137/113 |
| 1,938,369 A | * | 12/1933 | Beebe | 137/113 |
| 3,008,482 A | * | 11/1961 | Hunter | 137/113 |
| 4,162,146 A | * | 7/1979 | Seibert | 96/113 |
| 4,592,741 A | | 6/1986 | Vincent | |
| 4,654,029 A | * | 3/1987 | D'Antonio | 604/119 |
| 4,774,121 A | * | 9/1988 | Vollenweider, II | 428/117 |
| 4,889,531 A | * | 12/1989 | D'Antonio et al. | 604/319 |
| 5,429,663 A | * | 7/1995 | Cassidy et al. | 95/21 |

FOREIGN PATENT DOCUMENTS

| | | |
|---|---|---|
| EP | 0003022 A1 | 7/1979 |
| JP | 58099566 | 6/1983 |
| JP | 63006276 | 1/1988 |
| JP | 07148256 | 6/1995 |
| JP | 07-194691 | 8/1995 |
| WO | 2004/110523 A1 | 12/2004 |

OTHER PUBLICATIONS

Cerfolio, R.J., et al., "Prospective Randomized Trial Compares Suction Versus Water Seal for Air Leaks", Ann Thorac Surg, 2001, 71:1613-1617.

* cited by examiner

*Primary Examiner* — Tatyana Zalukaeva
*Assistant Examiner* — Ginger T Chapman
(74) *Attorney, Agent, or Firm* — McDonnell Boehnen Hulbert & Berghoff LLP

(57) ABSTRACT

A drainage device useable for treating patients with a pulmonary air leak, the device comprising suction mode control means, where a pressure sensor is connected to the suction mode control means for supplying a pressure signal representative of the pressure in a collection chamber, and an air flow sensor is connected to the suction mode control means to supply a flow signal representative of the flow of air evacuated from the collection chamber, and in that the suction mode control means is arranged to switch between a first suction mode and a second suction mode based on an algorithm involving the flow signal and the pressure signal.

6 Claims, 5 Drawing Sheets

PLEURAL DRAINAGE DEVICE AND VALVE FOR SUCH

FIELD OF THE INVENTION

The present invention relates to the field of medical technology. More particularly it relates to devices for pleural drainage used to aiding a collapsed lung after injury or surgery to recuperate by draining pleural cavity of excess fluid and air resulting from air leakage from injured lung and from fluid leaving the tissues in question. It also relates to a check valve for such a drainage device.

BACKGROUND OF THE INVENTION

A device for draining fluid and air from a patient's pleural cavity is known from e.g. WO04110523. Such devices apply a suction pressure in the patients pleural cavity via a tube from the patient's pleural cavity to the draining device. By the draining fluid and applying a pressure healing is improved. An objective of the present invention is to further improve the healing when using a drainage device by modifying the device.

SUMMARY OF THE INVENTION

The inventors have investigated the healing process and found that some patients at some point in time during their recovery may heal faster if active suction is replaced with what is referred to in the field as a "water seal". The inventors have further investigated what the problem actually is and thereafter developed a solution.

According to a first aspect the invention provides a drainage device useable for treating patients with a pulmonary air leak, said device comprising
- at least one airtight collection chamber having a first connection for a drainage tube, and a second connection for evacuation air from the airtight collection chamber;
- a pressure control unit connected to the second connection of the collection chamber for controlling an air pressure in the chamber;
- a pressure sensor capable of sensing the air pressure in the collection chamber;
- an air flow sensor capable of sensing the flow of air evacuated from the collection chamber where the drainage device is provided with a three way valve means for connecting the collection chamber via the second connection to the atmosphere or, to a suction source, and in that said device further is provided with means for calculating, based on a pressure sensor signal from the pressure sensor, and a flow sensor signal from the flow sensor, when it is suitable to rotate the three way valve means to shift from connecting the collection chamber to the suction source to connecting the collection chamber to the atmosphere, or vice versa.

According to a second aspect is provided a drainage device further provided with suction mode control means, where the pressure sensor is connected to the suction mode control means for supplying a pressure signal representative of the pressure in the collection chamber, and in that the air flow sensor is connected to the suction mode control means to supply a flow signal representative of the flow of air evacuated from the collection chamber, and in that the suction mode control means is arranged to switch between a first suction mode and a second suction mode based on an algorithm involving said flow signal and said pressure signal.

The suction mode control means may comprise a processor and a motor for controlling a three way valve.

The three way valve may be configured to switch between a position where the collection chamber is connected to atmospheric air, and a position where the collection chamber s connected to a suction pressure source.

A special ball valve may be controlled by the suction pressure controlled by the three way valve.

According to a further aspect is provided a method for a drainage device, the method comprising the following steps:
- reading a pressure signal from a pressure sensor arranged to sense pleural pressure;
- reading a flow signal from a flow sensor arranged to sense flow of air from a pulmonary air leak;
- creating a pressure difference value pD as difference between maximum of pressure signal and minimum of pressure signal during a certain period, suitably two minutes;
- creating a mean flow value by averaging flow signal during a certain period;
- deciding if pressure difference is less than a certain value, and at the same time the mean flow value is less than a certain value;
- if so, indicating that it is so;
- if not, indicating that it is not so.

According to still a further aspect is provided a method for a drainage device, the method comprising the following steps:
- reading a pressure signal from a pressure sensor arranged to sense pleural pressure;
- reading a flow signal from a flow sensor arranged to sense flow of air from a pulmonary air leak;
- creating a pressure difference value pD as difference between maximum of pressure signal and minimum of pressure signal during a certain period, suitably two minutes;
- creating a mean flow value by averaging flow signal during a certain period;
- deciding if pressure difference is less than a certain value, and at the same time the mean flow value is less than a certain value;
- if so applying a passive mode by rotating a three way valve to a passive suction position;
if not so, applying active suction by rotating the three way valve to an active suction position.

According to a last aspect of the invention is provided a special ball valve comprising a ball located and moveable between a first tube end and a second tube end, the tube ends are arranged to debouch in a common cavity, and also being arranged substantially opposite each other, and being provided with seats such that when a suction pressure is applied to one of the tubes the ball make contact to a seat and seals off that tube and leaves the other tube open to the cavity. The cavity may be provided with a further opening.

It should be emphasized that the term "comprises/comprising" when used in this specification is taken to specify the presence of stated features, integers, steps or components but does not preclude the presence or addition of one or more other features, elements, integers, steps, components or groups thereof.

Features that are described and/or illustrated with respect to one embodiment may be used in the same way or in a similar way in one or more other embodiments and/or in combination with or instead of the features of the other embodiments.

BRIEF DESCRIPTION OF THE DRAWINGS

The invention is described below with the aid of the following drawings in which:

FIG. 2d shows a drainage device similar to the one of FIG. 2a.

DETAILED DESCRIPTION OF PREFERRED EMBODIMENTS

Figure 1A:
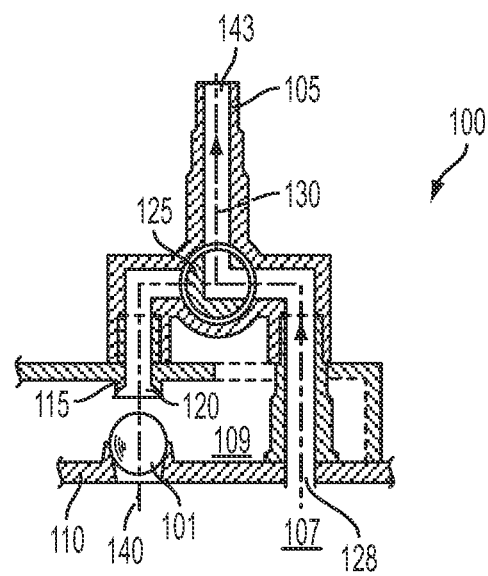
FIG. 1a shows a front cross sectional view of a check valve mechanism for switching between applying a suction pressure and applying a no pressure at all. The mechanism is in a mode of applying suction pressure.
Figure 1B:
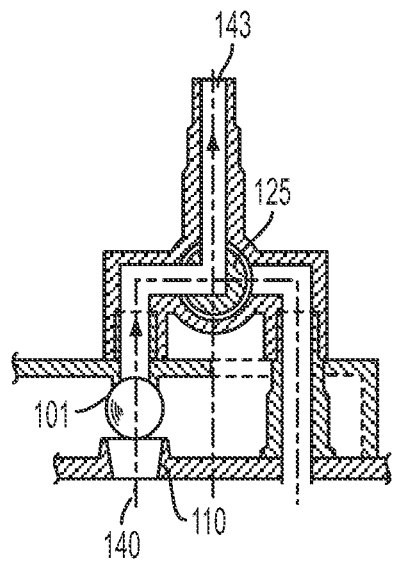
FIG. 1b shows the check valve mechanism of FIG. 1a in a mode of applying no pressure at all.

FIG. 1a shows a front cross sectional view of a check valve mechanism 100 for switching between applying a suction pressure and applying a no pressure at all. The mechanism is shown in a mode of applying suction pressure. The mechanism 100 comprises a first connection 105 for connection the mechanism 100 to a suction pressure source. Suction pressure is conveyed via channel opening 143 to a three way valve 125. Direction of flow of air is indicated by arrow 130. Three way valve 125 connects suction pressure to opening 128 or to ball valve upper opening 115 which is provided with a seat 120 being able cooperate with a ball 101 to seal off the ball valve upper opening 115 and, when doing this, open a ball valve lower opening 110 by sucking the ball towards the upper opening 115, as can be seen in figure 1b. The upper opening 115 and the lower opening 110 are preferably arranged opposite each other on a common axis 140. A common cavity 107 is in this way connected to either suction pressure from a suction pressure source or to a ball valve cavity 109, which in turn is connected to open air. The ball is preferably manufactured in a material having suitable density for being able to be maneuvered by suction pressure in spite of simultaneously being affected by gravity. This material could be massive or hollow plastic.

FIG. 1b shows the check valve mechanism of FIG. 1a in a mode of applying no pressure at all, the three way valve is set in a position to connect suction pressure to the ball valve upper opening thereby manoeuvring the ball to open the common cavity 107 towards open air.

Figure 1C:
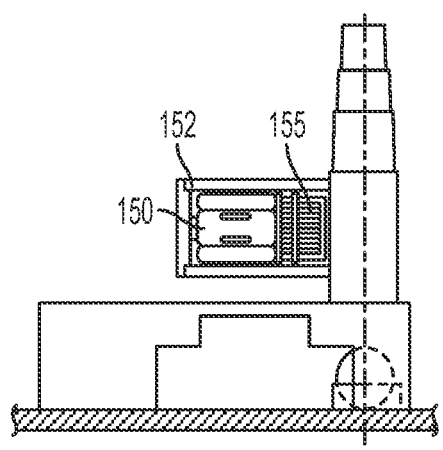
FIG. 1c shows in a side view the mechanism of FIG. 1 were a motor drive unit is clearly visible.

FIG. 1c shows in a side view the mechanism of FIG. 1 were a motor drive unit 150, 152, 155 is clearly visible. The motor drive unit comprises a frame 152 for holding an electric motor 150 and a gearbox 155 in a position for being able to actuate the three way valve 125.

Figure 2A:
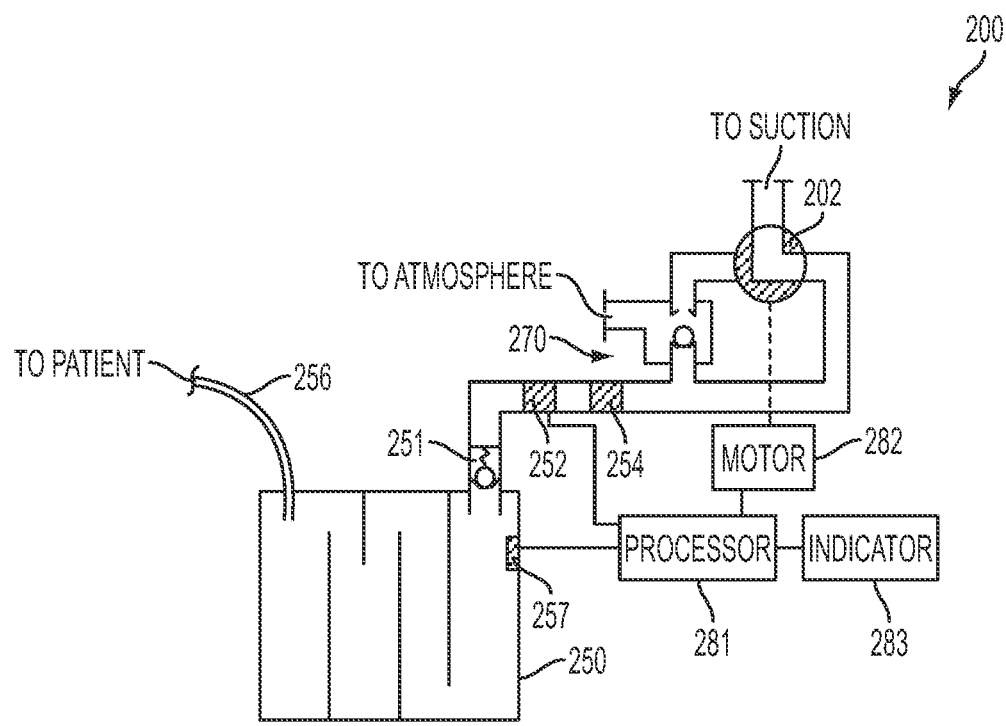
FIG. 2a shows a schematic diagram of a pleural drainage device making use of the mechanism of FIG. 1a-c.

FIG. 2a shows a schematic diagram of a pleural drainage device 200 making use of the mechanism of FIG. 1a-c. The drainage device comprises a suction tube 256 for connecting to a patient's pleural cavity, the tube is connected to a first opening of a collection chamber 250. A second opening of the collection chamber 250 is in turn arranged to be connected to a suction pressure source, not shown, or to the atmosphere via a three way valve 202. Preferably a one way valve 251, a flow sensor 252, and a pressure regulator 254 are arranged in conduits connecting the collection chamber 250 with the suction source or the atmosphere. The collection chamber 250 is provided with a pressure sensor 257 for sensing the pressure in the collection chamber 250. The drainage device is further provided with control means, e.g a processor 281 and a motor 282 for processing of the pressure and flow signals sensed by the pressure sensor 257 and the flow sensor 252. Based on the signals said control means 281, 282 would control the position of the three way valve based on pressure sensor signals and flow sensor signals as will be explained below. In another preferred embodiment the device is provided with an indicator 283 for indicating when the position of the three way valve should be changed, i.e., when drainage suction mode should be shifted from "active suction mode" to "passive suction mode".

The drainage device is preferably provided with a special ball valve 270. An advantage of providing a special ball valve is that the pressure a patients breathing musculature has to create to overcome flow resistance of the drainage device when the drainage device is in a "passive mode", i.e., the collection chamber is connected to the atmosphere, becomes lower than otherwise.

Figure 2B:
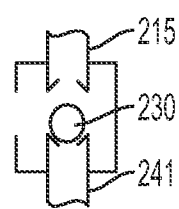
FIGS. 2b and 2c shows a detail of a special ball valve.
Figure 2C:
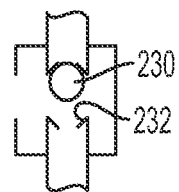

Referring to FIGS. 2b and 2c, the function of the special ball valve is that in a first position of the ball 230, as seen in FIG. 2b, seat 232 together with the ball 230 seals off the tube 241 such that there is no connection to the atmosphere as long as there is negative pressure, i.e., suction pressure in tube 241 that is connected to the collection chamber. In case of positive pressure in tube 241 the ball and seat functions as an over-pressure valve and let positive pressure out. In FIG. 2c the ball 230 is in a second position because suction pressure of tube 215 lifts the ball 230 to seal off tube 215. The passage of tube 241 becomes free to the atmosphere.

Figure 2D:
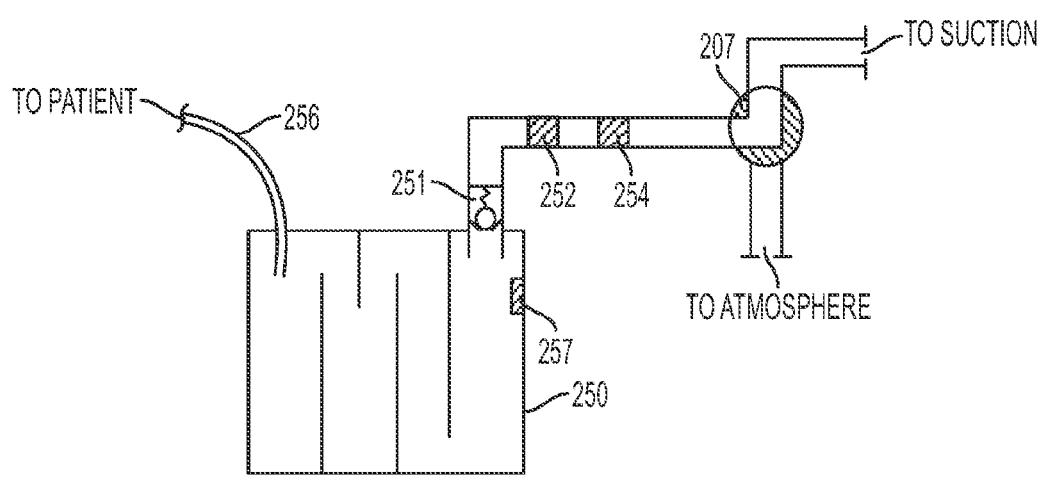

FIG. 2d shows a drainage device very similar to the one of FIG. 2a. The processor, motor and indicator have been omitted for clarity. A three way valve 207 is arranged to connect the collection chamber 250 to a suction source when in a first position, or to the atmosphere when rotated to a second position.

In still a further embodiment (not shown) the motor may be omitted for reducing production costs. Medical staff can rotate three-way valve manually if it is provided with suitable handle, instructed so by the indicator. Such omitting can be applied both to the devices of FIG. 2a and FIG. 2d.

However, it is foreseen to be more advantageous if switching is performed automatically as described above, without delay.

Figure 3:
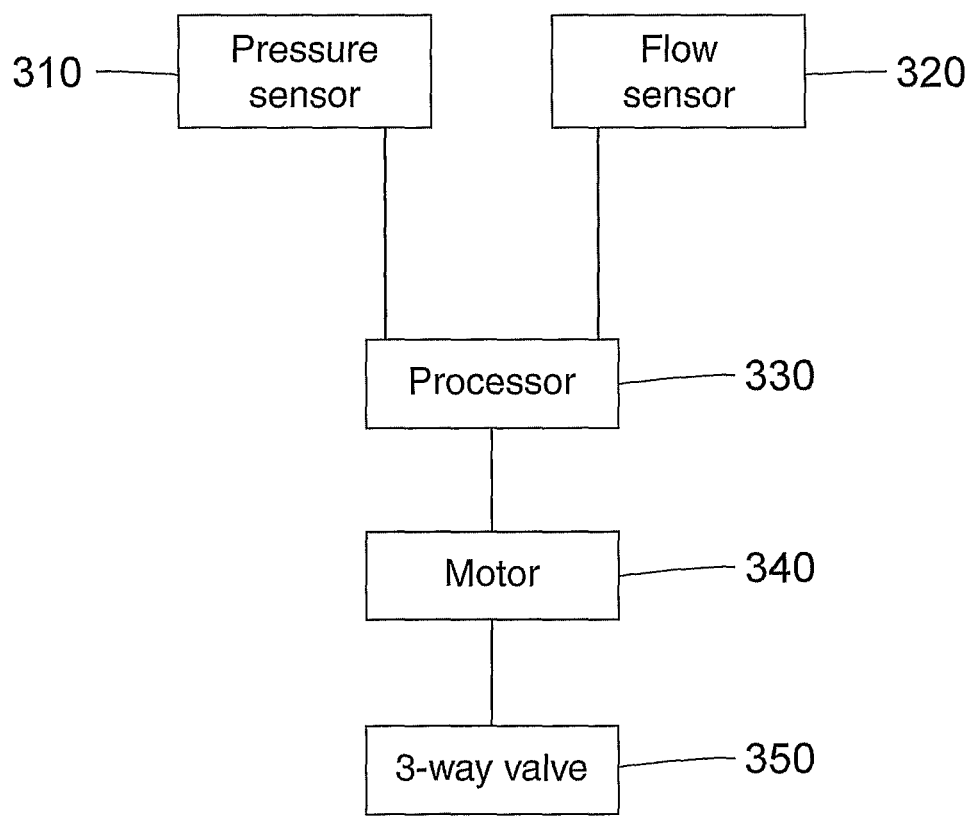
FIG. 3 is a block diagram showing main units for controlling a drainage device in accordance with an embodiment of the invention.

FIG. 3 is a block diagram showing main units for controlling a drainage device in accordance with an embodiment of the invention. A pressure sensor 310 and a flow sensor 320 are connected to a processor 330. The processor 330 processes signals from the sensors and outputs control signals to a motor 340 connected to the processor 330 to rotate a three way valve 350 mechanically connected to the motor.

Figure 4:
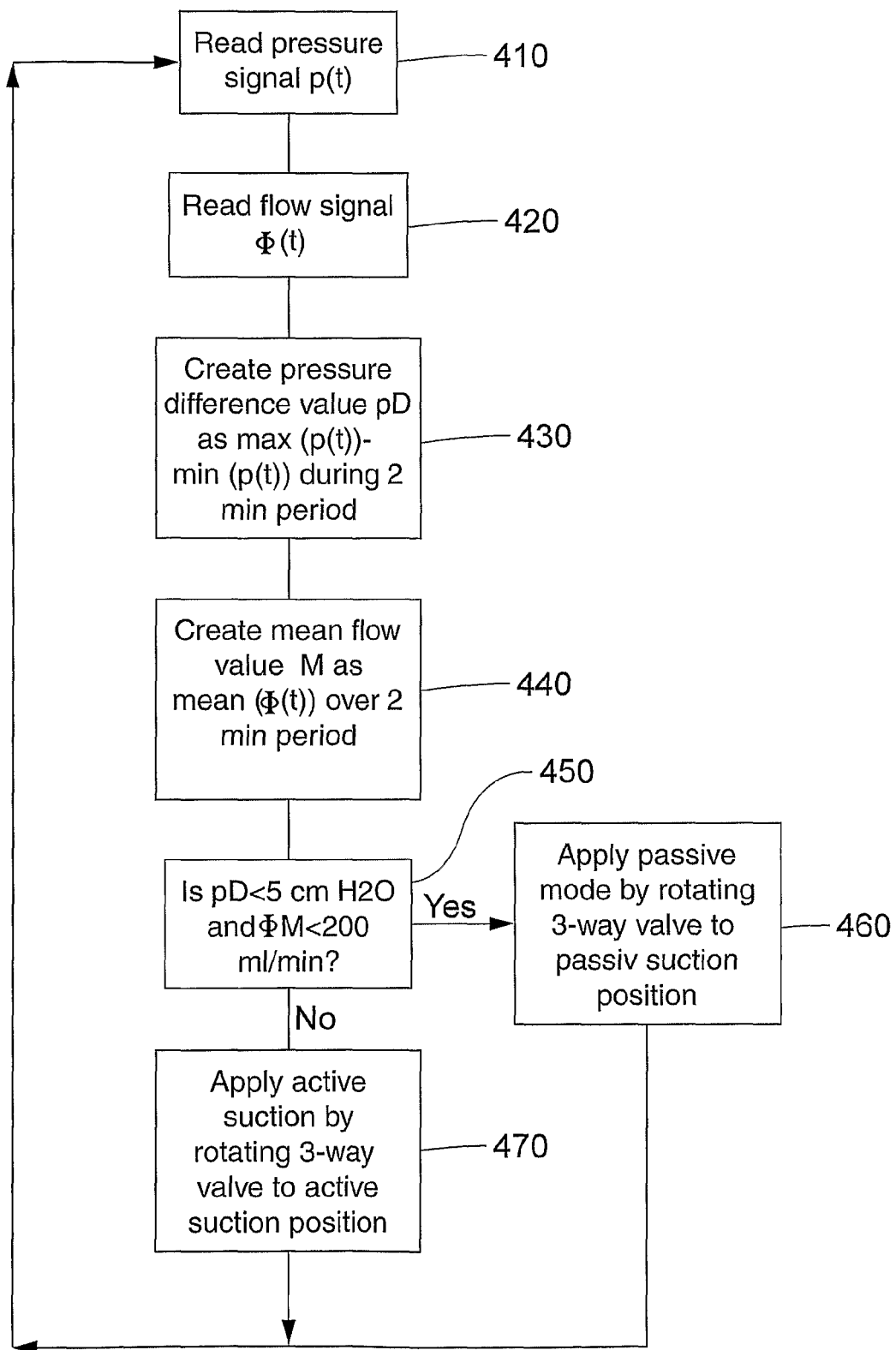
FIG. 4 is a flowchart showing a method of controlling the suction mode of a drainage device

FIG. 4 is a flowchart showing a method of controlling the suction mode of a drainage device. The method comprising the following steps reading 410 pressure signal from pressure sensor 310;

reading 420 flow signal from flow sensor 320;

creating 430 pressure difference value pD as a difference between maximum of pressure signal and minimum of pressure signal during a certain period, suitably two minutes;

creating 440 mean flow value by averaging flow signal during a certain period, suitably two minutes;

deciding 450 if pressure difference is less than a certain value, suitably 5 cm water column and at the same time the mean flow value is less than a certain value, suitably 200 ml per minute;

if so applying 460 passive mode by rotating three way valve to passive suction position;

if not so, applying 470 active suction by rotating three way valve to active suction position.

In another embodiment is provided a method for indication on an indicator that it is a suitable point in time to manually switch suction mode on a drainage device with a manually operated three way valve, the method comprising the following steps:

reading pressure signal from pressure sensor 310;

reading flow signal from flow sensor 320;

creating pressure difference value pD as a difference between maximum of pressure signal and minimum of pressure signal during a certain period, suitably two minutes;

creating mean flow value by averaging flow signal during a certain period, suitably two minutes;

deciding if pressure difference is less than a certain value, suitably 5 cm water column and at the same time the mean flow value is less than a certain value, suitably 200 ml per minute;

if so indicating, e.g., by means of a coloured first light emitting diode, that it is a suitable point in time to apply passive mode;

if not so, indicating e.g., by means of a second light emitting diode that suction should be kept in active mode.

It should be understood that indication of if it is suitable to switch from active to passive suction mode, or vice versa, could be achieved by any suitable device connectable to a processor, e.g., a display or a buzzer or other light or sound generating organ.

The invention claimed is:

1. A drainage device useable for treating patients with a pulmonary air leak, said device comprising:

at least one airtight collection chamber having a first connection for a drainage tube, and a second connection for evacuation air from the airtight collection chamber;

a pressure control unit connected to the second connection of the collection chamber for controlling an air pressure in the chamber;

a pressure sensor capable of sensing the air pressure in the collection chamber;

an air flow sensor capable of sensing a flow of air evacuated from the collection chamber;

wherein said drainage device is provided with a three way valve means configured to switch between a first position where the collection chamber is connected to a suction source via the second connection and the collection chamber is disconnected from an atmosphere, and a second position where the collection chamber is connected to the atmosphere, and the collection chamber is disconnected from the suction source, and wherein said device further is provided with means for calculating, based on a pressure sensor signal from the pressure sensor, and a flow sensor signal from the flow sensor, when it is suitable to rotate the three way valve means to shift from connecting the collection chamber to the suction source to connecting the collection chamber to the atmosphere, or vice versa;

a ball valve comprising a ball located and moveable between a first tube end and a second tube end, the tube ends are arranged to debouch in a common cavity, and also being arranged substantially opposite each other, and being provided with seats such that when a suction pressure is applied to one of the tubes the ball makes contact to a seat and seals off that tube and leaves the other tube open to the cavity.

2. The drainage device of claim 1 further comprising a suction mode control means, where said pressure sensor is connected to said suction mode control means for supplying a pressure signal representative of the pressure in the collection chamber, and wherein said air flow sensor is connected to said suction mode control means to supply a flow signal representative of the flow of air evacuated from the collection chamber, and in that said suction mode control means is arranged to switch between a first suction mode and a second suction mode based on an algorithm involving said flow signal and said pressure signal.

3. The drainage device according to claim 1 where said suction mode control means comprises a processor and a motor for controlling the three way valve.

4. The drainage device according to claim 3, where the ball valve is controlled by the suction pressure controlled by the three way valve.

5. The drainage device of claim 1 where the cavity is provided with a further opening.

6. The drainage device of claim 1 further comprising a check valve mechanism comprising a ball valve, in turn comprising a ball located and moveable between a first tube end and a second tube end, the tube ends being arranged to debouch in a cavity, and also being arranged substantially opposite each other, and being provided with seats such that when a suction pressure is applied to one of the tubes the ball makes contact to a seat and seals off that tube and leaves the other tube open to the cavity, and wherein the cavity is provided with a further opening to atmosphere, and wherein the check valve mechanism further comprises a three way valve arranged to connect suction pressure via first tube end to ball valve upper opening, or, simultaneously to ball valve lower opening and a common cavity to be connected to a patient's pleural cavity.

\* \* \* \* \*